United States Patent [19]

Stephens

[11] 3,933,894

[45] Jan. 20, 1976

[54] N-ARYLSULFONYL CARBAMATES

[75] Inventor: John A. Stephens, St. Louis County, Mo.

[73] Assignee: Monsanto Company, St. Louis, Mo.

[22] Filed: Dec. 10, 1973

[21] Appl. No.: 423,330

Related U.S. Application Data

[60] Division of Ser. No. 547,376, May 3, 1966, Pat. No. 3,799,760, which is a continuation-in-part of Ser. No. 266,513, March 20, 1963, abandoned, which is a continuation-in-part of Ser. No. 256,840, Feb. 7, 1963, abandoned.

[52] U.S. Cl. .................................. 260/470; 71/103
[51] Int. Cl.² ...................................... C07C 149/40
[58] Field of Search ................................ 260/470

[56] References Cited
UNITED STATES PATENTS

3,806,542    4/1974    Werner .............................. 260/470

*Primary Examiner*—Lorraine A. Weinberger
*Assistant Examiner*—L. A. Thaxton
*Attorney, Agent, or Firm*—William I. Andress

[57] ABSTRACT

The present invention relates to amine, alkali metal and alkaline earth metal salts of N-benzene sulfonyl carbamic acid esters and to lower alkenyl N-benzene sulfonyl carbamates. These compounds are useful as herbicides.

4 Claims, No Drawings

N-ARYLSULFONYL CARBAMATES

This is a division of application Ser. No. 547,376, filed May 3, 1966, now U.S. Pat. No. 3,799,760, which is a continuation-in-part of application Ser. No. 266,513, filed Mar. 20, 1963, which, in turn, is a continuation-in-part of application Ser. No. 256,840, filed Feb. 7, 1963, both now abandoned.

This invention relates to methods for controlling and protecting plant life by the application of N-arylsulfonyl carbamate esters or by the application of the amine or metal salts of N-arylsulfonyl carbamate esters. The invention further relates to certain N-arylsulfonyl carbamate esters and their amine and metal salts as novel compositions of matter.

In recent years, the use of chemicals for controlling various biological forms has found widespread acceptance among many people. This is especially true among agriculturalists interested in controlling plant systems and insect pests. For example, chemical compositions have previously been applied to the soil or to the foliage of fully developed plants, thereby destroying certain types of plants in a selective manner and allowing others to continue their growth in a more favorable environment. This type of control, enabling certain plants to grow freely unhampered by competing noxious plants, has also been achieved by the application of chemical compositions to the soil, which chemical compositions either prevent germination of undesirable seeds or destroy the emerging seedlings immediately after germination. Other dangers confronting plant growth and crop yields occcur in the form of insect pests and plant diseases. These threats to desirable plant life have been lessened by the application of insecticides and fungicides to the soil, foliage of the plants, and surrounding atmosphere.

It is an object of this invention to provide novel methods for inhibiting the growth of plant life. It is a further object of this invention to provide certain N-arylsulfonyl carbamate esters as novel compositions of matter. It is a further object of this invention to provide certain amines and metal salts of N-arylsulfonyl carbamate esters as novel compositions of matter. It is yet another object of this invention to provide methods for both pre-emergence and post-emergence control of undesirable plant life. Additional objects, benefits and advantages will become apparent as the detailed description of the invention proceeds.

The compounds useful in the practice of the present invention are those having the molecular configuration:

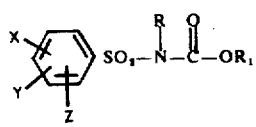

where X, Y, and Z are selected from the group consisting of hydrogen, chloro, bromo, iodo, nitro, and lower alkyl; where R is selected from the group consisting of hydrogen, alkyl, cycloalkyl, alkenyl, alkynyl, aryl, alkaryl, aralkyl, and acyl, and where $R_1$ is selected from the group consisting of alkyl, cycloalkyl, alkenyl, alkynyl, aryl, alkaryl, aralkyl, and acyl.

Compounds of this invention are useful as herbicides. The herbicidal activity can be demonstrated by contacting a plant structure with the compound, which may take place either pre-emergently or on established plants. Pre-emergence application may be accomplished in either of two ways - by application of the compounds to the surface of the soil or by incorporation of the compounds into the surface layer of soil. Depending upon the particular plants to be controlled, the compounds of this invention may exhibit more activity in one type of application than in another. Post-emergence application is usually carried out by contacting the foliage of the plants with the compounds although application in the soil in the vicinity of the plants can also have some beneficial effect. Some of the compounds possess activity both as pre-emergence and post-emergence herbicides. Hence, the user can benefit from the application of some compounds in a dual manner, depending upon which compound or mixture of compounds are selected.

The N-(arylsulfonyl) carbamates useful in the practice of this invention may contain an unsubstituted benzene ring attached to the sulfonyl group, as for example, ethyl N-(benzenesulfonyl) carbamate. The present invention also encompasses compounds containing substituents on the aromatic ring in either the ortho, meta, or para position. Furthermore, combinations of ortho and meta, ortho and para, meta and para, and ortho, meta and para substitutions are within the scope of this invention, as well as di-ortho and di-meta combinations. These substitutions on the ring may consist of halogen atoms, particularly chlorine, of nitro radicals, and of lower alkyl radicals such as methyl, ethyl, propyl, isopropyl, n-butyl, isobutyl, sec-butyl, tert-butyl, n-amyl, isomeric amyl, n-hexyl, and isomeric hexyl radicals. In addition, mixed substitutions on the aromatic ring such as 3-nitro, 4-chloro and 2-methyl, 4-chloro provide compounds within the scope of this invention. Common and easily prepared substitutions on the aromatic ring comprise 2,4,2,6; and 2,4,6 combinations. In the series $RSO_2NHCOOC_2H_5$ where R is an aryl radical, general herbicidal activity was increased with variation of R as follows:

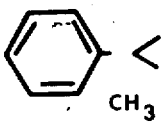 

Compounds illustrative of these many possible substitutions include: ethyl N-(p-toluenesulfonyl) carbamate; ethyl N-(o-toluenesulfonyl) carbamate; ethyl N-(2,6-dichlorobenzenesulfonyl) carbamate; ethyl N-(2-chloro-p-toluenesulfonyl) carbamate, ethyl N-(m-nitrobenzenesulfonyl) carbamate; ethyl N-(3,4-dichlorobenzenesulfonyl) carbamate; ethyl N-(2,4,6 trichlorobenzenesulfonyl) carbamate, and ethyl N-(p-cumenesulfonyl) carbamate.

The substituent attached to the nitrogen atom, R in the general formula, can be either hydrogen or alkyl, cycloalkyl, alkenyl, alkynyl, aryl, alkaryl, aralkyl, or acyl, preferably containing not more than eight carbon atoms and more preferably not more than four carbon atoms. These radicals may be either straightor branchchained. Examples of suitable compounds include: ethyl N-(benzenesulfonyl) N-(methyl) carbamate;

ethyl N-(benzenesulfonyl) N-(benzyl) carbamate; ethyl N-(benzenesulfonyl) N-(n-butyl) carbamate; ethyl N-(benzenesulfonyl) N-(isopropyl) carbamate; ethyl N-benzenesulfonyl) N-(p-ethylbenzene) carbamate; ethyl N-(benzenesulfonyl N-(p-cumene) carbamate; ethyl N-(benzenesulfonyl) N-(allyl) carbamate; and ethyl N-(benzenesulfonyl) N-(acetyl) carbamate.

The ester group, $R_1$ in the generic formula, is capable of variation similar to the nitrogen substituent R, insofar as it can be alkyl, cycloalkyl, alkenyl, alknynyl, aryl, alkaryl, aralkyl, or acyl, preferably containing not more than eight carbon atoms. These groups may also be either straight- or branch-chained. In the series

where R = alkyl, activity was increased with the following changes in R:

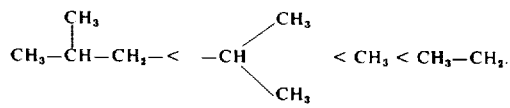

Examples of compounds illustrative of this variation include: methyl N-(benzenesulfonyl) carbamate; isopropyl; N-(benzenesulfonyl) carbamate; vinyl N-(benzenesulfonyl) carbamate; allyl N-(benzenesulfonyl) carbamate; tert-butyl N-(benzenesulfonyl) carbamate; benzyl N-(benzenesufonyl) carbamate; and phenyl N-(benzenesulfonyl) carbamate.

N-(arylsulfonyl)carbamates are strongly acidic materials which form stable salts with amines or inorganic bases. These salts are also useful in various aspects of plant control. Examples of such salts include: ethyl N-(benzenesulfonyl) carbamate salt of cyclohexylamine and 2-dimethylaminoethyl-p-nitrobenzenesulfonyl carbamate salt of N,N-dimethylaminoethanol. The alkali metal and alkaline earth metal salts of the N-(arylsulfonyl) carbamates are also easily prepared by reacting the subject carbamates with the selected basic material such as NaOH, $Na_2CO_3$, KOH, and $Ca(OH)_2$. Preferred amine salts are the secondary amine salts; preferred metal salts are the sodium, calcium and magnesium salts. The amine and metal salts are stable, easy to handle, and in general possess a biological toxicity equal to that of the parent carbamate. In some cases, certain types of biological activity may even be enhanced by conversion of the carbamate to the metal or amine salt.

Two general methods were used to prepare N-(arylsulfonyl) carbamates - the reaction of the corresponding sulfonamide with suitable chlorocarbonate in (1) dry acetone in the presence of anhydrous potassium carbonate or in (2) aqueous alkali. The preparation of amine and inorganic salts was accomplished by dissolving the N-(arylsulfonyl) carbamate in dry ether and adding a suitable amine also dissolved in ether, or an inorganic base dissolved in an ether-miscible solvent.

In the preparation of the above-mentioned carbamates by the first method, the reaction proceeded in the following manner:

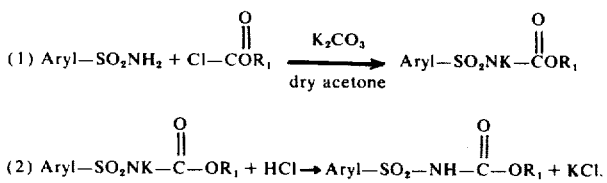

In the first step, a chlorocabonate is added to a mixture of a selected arylsulfonamide and powdered anhydrous potassium carbonate in dry acetone, Relative quantities of the reactants are not critical, but a good yield of product based upon the percent of arylsulfonamide converted to the carbonate can be achieved by using quantities of the chlorocarbonate and potassium carbonate in excess of the stoichiometric amount. Acetone sufficient to dilute the reactants is used. The chlorocarbonate should be added slowly over a period of several minutes with vigorous stirring to prevent re-precipitation of the sulfonamide. After addition, the mixture is heated to reflux temperature and held at this temperature for an hour or more. I have found 5–6 hours to be sufficient for most of my experimentation, but a shorter or longer time may be desirable, depending upon the reactants and the percent yield desired. After cooling, the slurry formed by the reaction is allowed to stand at room temperature for a period of time, overnight if convenient. Upon standing, a white solid is formed which can be collected on a filter and washed with acetone. This solid material is then dissolved in water, and the solution may be filtered and extracted with ether. In the second step of the preparation, the solution should be cooled to a temperature which will permit a satisfactory rate of reaction — cooling to 0°C in an ice bath is suggested — and treated with an excess of concentrated mineral acid to liberate the crude product. The product at this point may be extracted with a suitable water-immiscible solvent such as ethyl ether or benzene. The solvent and extracted product are then dried over a dessicant such as $CaSO_4$ or $MgSO_4$, and the solvent subsequently removed under reduced pressure. If a highly purified product is required, the product may be re-crystallized from a suitable solvent.

In the preparation of N-(arylsulfonyl) carbamates in an aqueous alkali medium, the reaction proceeds in the following manner:

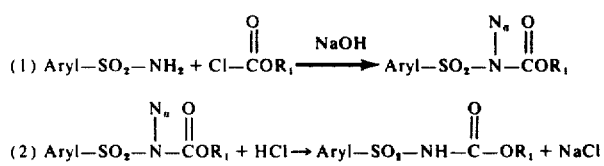

In the first step of the preparation, a selected sulfonamide is dissolved in an aqueous solution containing a quantity of an alkali metal base such as NaOH or KOH slightly in excess of the amount necessary for complete reaction with the sulfonamide. The solution is then filtered to remove reprecipitated sulfonamide and cooled to around 15°C. A chlorocarbonate and a 10% aqueous solution of an alkali metal base are then added slowly with stirring, the rate of addition being adjusted so that no precipitate is formed. Stirring at room temperature for several hours is recommended; overnight stirring is satisfactory. The solution is filtered to remove any solids, and the filtrate then cooled to 10° or 15°C and acidified with dilute (5–20%) HCl to a slightly alkaline condition. Stirring for several minutes to allow complete reaction is desirable. Any solid formed in this step is filtered off and the filtrate further acidified to a slightly acid condition. Again any formed solid is filtered off and the filtrate cooled to 5°–10°C. Further acidification to pH 1 or 2 is effected with concentrated (12M) HCl. Stirring for around two hours at 5°–10°C is suggested to insure a maximum yield of product. The white solid may then be filtered, washed with water, dried in air, and recrystallized from a suitable solvent such as ethyl ether.

The advantages and benefits of the present invention will become more fully understood when interpreted in view of the detailed description set forth in the following examples.

EXAMPLE I

A quantity of 51.5 grams (0.30 mole) of p-toluenesulfonamide was added to 132 grams of 10% NaOH (0.30 mole) diluted with 100 ml of water. Nearly complete solution was achieved. The solution was cooled to 16°C. A small portion of the 32.5 gram (0.30 mole) quantity of ethyl chlorocarbonate was added to the solution, causing the formation of a small amount of precipitate. To prevent the formation of precipitate, 10% NaOH was added as required. The remainder of the ethyl chlorocarbonate was added slowly over a period of 90 minutes. The solution was stirred for six hours as 10% NaOH was added to maintain solution of the components. The temperature of the solution was maintained between 16° and 19°C throughout this part of the experiment. At the end of 6 hour stirring period, the solution was allowed to stand overnight at room temperature. The total amount of 10% NaOH added was 375 grams. After standing, the solution was filtered to remove 2.5 grams of solid material. The filtrate was partially acidified by slow addition of dilute HCl (15.4 grams of concentrated 12M HCl diluted to 50 ml. with water). A quantity of 19.8 grams of solid material formed which was removed by filtration. The filtrate was then treated with more dilute HCl to bring the pH down to around pH 8. This caused the formation of 1.2 grams of solid which was removed by filtration. To this filtrate, 30.8 grams of concentrated HCl was added slowly with stirring. A white precipitate formed around pH 5 with 15 ml. of acid still to be added. After the acid was added, the pH was 3.5 and a white oil had separated from the solution. This oil solidified on cooling to room temperature. The filtered precipitate was washed with water and dried in air. This material was ethyl N-(p-toluenesulfonyl) carbamate. Weight of the material was 30.1 grams which represented a 41.2% yield. Softening point was 75°C; melting point was 79°–81°C. After a crystallization from a benzene-hexane solvent, the softening and melting points were unchanged. The prepared compound was identified as ethyl n-(p-toluenesulfonly) carbamate

EXAMPLE II

A quantity of 42.7 grams (0.20 mole) of N-n-butyl-benzenesulfonamide was dissolved in 100 grams (1.0 molel) of triethylamine. To this solution 28 grams (0.26 mole) of ethyl chloroformate was added slowly with stirring over a 70 minute period. The solution was cooled as necessary to maintain the temperature around 20°C. During the addition of the chloroformate, a pink slurry was formed and there was also a noticeable evolution of gas. After addition of the chloroformate, stirring was discontinued but the reaction mixture was allowed to remain in the cooling bath at 20°C for an additional 2.5 hours. After standing overnight at room temperature, the mixture was filtered and 23.5 grams of pink solid material was removed from the mixture. Excess solvent was removed from the filtrate by evaporation at 65°C and 9 mm pressure. An orange oily residue remained which was cooled to 20°C, stirred, and treated with 50 ml. 10% NaOH. About 100 ml. of ether was added and the mixture stirred for an additional 10 minutes. When the stirring was stopped, the ether layer was separated from the aqueous layer, washed successively with water, 10% HCl, water, and saturated NaCl solution, and then dried over $MgSO_4$. Solvent was evaporated at 70°C and 14 mm. pressure. The prepared compound was identified as ethyl N-(benzenesulfonyl) N-(n-butyl) carbamate. Weight of the product was 48.5 grams which represented a yield of 85.2%; $n_D^{25}$ 1.5064. Treatment with HCl was unnecessary since a carbamate such as this with no available hydrogen attached to the nitrogen does not form a salt requiring neutralization to form the desired product. The 10% HCl wash used above was used only to remove entrained NaOH or $K_2CO_3$.

EXAMPLE III

A quantity of 50 grams (0.29 mole) of o-toluenesulfonamide was dissolved in 140 grams of 10% NaOH. This mixture was diluted with 100 ml. of water to obtain a nearly complete solution. The solution was cooled to 15°C. Ethyl chlorocarbonate (33 g., 0.30 mole) was added slowly with stirring along with sufficient 10% NaOH to maintain solution of the sulfonamide. After the chlorocarbonate was added, the solution was stirred at this reduced temperature for approximately an hour. The solution was allowed to stand overnight at room temperature. Total NaOH used was 38.1 grams (0.96 mole). The solution was filtered to remove 13.7 grams of solid material. Dilute HCl (17.5 grams of 12M HCl diluted to 50 ml. with water) was added to the filtrate with stirring. Solid precipitated by this addition (19.1 grams) was removed by filtration and another 50 ml. quantity of dilute HCl was added to the filtrate. No precipitate was formed. An additional 35 grams of concentrated HCl was added and a white precipitate formed which was filtered, washed with water, and dried. The product was identified as ethyl N-(o-toluenesulfonyl) carbamate. Weight of product was 17.5 grams which represented a yield of 24.5%. Softening point was 115°C; melting point was 117°–119°C.

EXAMPLE IV

Ethyl N-(p-chlorobenzenesulfonyl) carbamate was prepared by reacting p-chlorobenzenesulfonamide (29 grams, 0.15 mole) with ethyl chlorocarbonate (21 grams, 0.19 mole) in the presence of 10% aqueous NaOH according to the procedure described in Example III. Weight of the final product was 13.4 grams, which represented a yield of 34%. Softening point was 86°C; melting point was 89°–91°C. Upon recrystallization from a benzene-hexane solvent, the softening point was 90°C; melting point was 92°–93°C. Calculated nitrogen content was 5.31%, found 5.61%.

EXAMPLE V

Ethyl N-(p-nitrobenzenesulfonyl) carbamate was prepared by reacting p-nitrobenzenesulfonamide (30.2 grams, 0.15 mole) with ethyl chlorocarbonate (21 grams, 0.19 mole) in the presence of 10% aqueous NaOH according to the procedure described in Example III. Weight of the final product was 25.8 grams, which represented a yield of 62.8%. Melting point was 130°–132°C. A quantity of 49 grams of p-toluenesulfonamide (0.29 mole) was added to a slurry consisting of 56.5 grams (0.41 mole) of anhydrous $K_2CO_3$ in 500 ml. of dry acetone. Ethyl chlorocarbonate (42 grams, 0.39 mole) was added slowly with stirring. This mixture was refluxed for 5 hours and allowed to stand overnight at room temperature. A white solid which had formed was removed and the acetone filtrate was evaporated leaving a tan gummy solid. The white solid was dissolved in 750 ml. water and cooled in ice. The solution was acidified to pH 2 with 40 ml. concentrated HCl to precipitate a while oil. This mixture was extracted three times with 50 ml. portions of ether. Upon evaporation of the ether, a hard white solid remained. This solid was identified as ethyl N-(p-toluenesulfonyl) carbamate. Weight of the product was 58 grams which represented an 82.3% yield. Melting point was 81°–83°C. This product is identical with the product of Example I. HOwever, the yield in this example was far superior. Biological properties were the same.

EXAMPLE VII

A quantity of 20 grams (0.071 mole) of N-benzyl p-chlorobenzenesulfonamide was added to a slurry of 18.8 grams (0.136 mole) of anhydrous $K_2CO_3$ in 210 ml. of acetone. 2-Chloroethyl chlorocarbonate (18.7 grams, 0.131 mole) was added slowly with stirring. The mixture was refluxed for 5 hours and then allowed to stand overnight. A white solid which formed was removed by filtration. The acetone filtrate was evaporated, leaving a gummy white residue. This residue was dissolved in 200 ml. ether and extracted twice with 40 ml. portions of 10% NaOH and once with 100 ml. water. The filtrate was evaporated to leave a white solid. It was necessary to react the acetone filtrate with HCl since a carbamate such as this with no available hydrogen attached to the nitrogen does not form a salt requiring neutralization. The white solid left after evaporation of the ether is the product 2-chloroethyl N-(p-chlorobenzenesulfonyl) N-benzyl carbamate. Weight of the product was 27.5 grams which represented a 100% yield. Calculated analysis of this compound was C 49.49%, H 3.87%, N 3.51%; found C 49.47%, H 4.01%, N 3.58%. Sintering point was 128°C; melting point was 129°–130°C.

EXAMPLE VIII

A quantity of 22.6 grams (0.10 mole) of 3,4-dichlorobenzenesulfonamide benzenesulfonamide was added to a slurry of 15 grams $K_2CO_3$ in 150 ml. of dry acetone. Allyl chlorocarbonate (12.5 grams, 0.105 mole) was added slowly with stirring. This mixture was refluxed for five hours and then allowed to stand overnight at room temperature. The solution was filtered to remove 11.5 grams of solid material. The acetone solvent was evaporated from the filtrate, leaving behind a yellow gummy residue. This residue was treated with 10 grams $NaHCO_3$ in 100 ml. water to form a white solid, which was filtered and dried. The bicarbonate extract was extracted with 50 ml. ether and the separated aqueous layer was acidified to pH 2 with concentrated HCl. A gummy white material formed. This mixture was extracted twice with 50 ml. ether. The ether extract was heated to remove ether, leaving a white solid. This product was identified as allyl N-(3,4-dichlorobenzenesulfonyl) carbamate. Weight of the product was 5.7 grams which represented a 19% yield. Sintering point was 83°C; melting point was 85°–87°C. Product was very soluble in benzene, acetone, and ether; it was insoluble in water and hexane. Upon recrystallization from benzene-hexane, the melting point and solublity characteristics were unchanged.

EXAMPLE IX

Allyl N-(m-nitrobenzenesulfonyl) carbamate was prepared by reacting 20.2 grams (0.10 mole) of m-nitrobenzenesulfonamide with 12 grams (0.10 mole) of allyl chlorocarbonate in the presence of anhydrous $K_2CO_3$ in acetone according to the procedure described in Example VI. The product was a pale yellow oil which solidified on cooling. Weight of the final product was 5 grams which represented a yield of 17.8%. Melting point was 84°–86°C.

EXAMPLE X

Allyl N-(p-chlorobenzenesulfonyl) carbamate was prepared by reacting 19.1 grams (0.10 mole) of p-chlorobenzenesulfonamide with 12.5 grams (0.105 mole) of allyl chlorocarbonate in the presence of anhydrous $K_2CO_3$ in acetone according to the procedure described in Example VI. Weight of the final product was 16 grams, which represented a 58.3% yield. The product was a white gummy solid. Upon recrystallization from a $CHCl_3$-hexane solvent, the yield was 11.2 grams for a 41% yield. Melting point was 63°–65°C.

EXAMPLE XI

Allyl N-(p-toluenesulfonyl) carbamate was prepared by reacting 51.5 grams (0.30 mole) of p-toluenesulfonamide with 37 grams (0.30 mole) of allyl chlorocarbonate in the presence of anhydrous $K_2CO_3$ in acetone according to the procedure described in Example VI. Weight of the white solid product was 40 grams, which represented a 57.5% yield. Sintering point was 63°C; melting point was 67°–69°C.

EXAMPLE XII

Isopropyl N-(p-toluenesulfonyl) carbamate was prepared by reacting 13.5 grams (0.08 mole) of p-toluene sulfonamide with 16.0 grams (0.131 mole) of isopropyl chlorocarbonate in the presence of 18.8 grams (0.136 mole) of anhydrous $K_2CO_3$ and 200 ml. of dry acetone according to the procedure described in Example VI.

The product was a hard white solid, weighing 17.9 grams which represents a yield of 86.8%. Sintering point was 77°C; melting point was 78°–80°C.

EXAMPLE XIII

Isopropyl N-(p-chlorobenzenesulfonyl) carbamate was prepared by reacting 15.4 grams (0.08 mole) of p-chlorobenzenesulfonamide with 16.0 grams (0.131 mole) of isopropyl chloroformate in the presence of 18.8 grams (0.136 mole) of anhydrous $K_2CO_3$ and 200 ml. of dry acetone according to the procedure described in Example VI. The product was a hard white solid, weighting 18.6 grams which represents a yield of 83.8%. Sintering point was 87°C; melting point was 89°–91°C.

EXAMPLE XIV

Isopropyl N-(p-chlorobenzenesulfonyl) N-benzyl carbamate was prepared by reacting 20.0 grams (0.071 mole) of N-benzyl p-chlorobenzensulfonamide with 16.0 grams (0.131 mole) of isopropyl chlorocarbonate in the presence of 18.8 grams (0.136 mole) of anhydrous $K_2CO_3$ and 210 ml. dry acetone. After refluxing for 6 hours and standing overnight, the mixture was filtered to remove a white precipitate. The filtrate was evaporated to leave a gummy white solid. This residue was dissolved in 125 ml. warm isopropanol and the resulting solution added to 160 grams of 5% NaOH. The white solid which formed was filtered, washed with water, and dried. This solid was the carbamate product. Weight was 4.5 grams which represented a yield of 17.3%. Sintering point was 78°C; melting point was 80°–81°C. Calculated analysis was C 55.22%, H 4.92%, and N 3.81%; found by analysis was C 55.34%, H 4.92%, and N 3.69%.

EXAMPLE XV

Isopropyl N-(p-toluenesulfonyl) N-methyl carbamate was prepared by reacting 13.2 grams (0.071 mole) of N-methyl p-toluenesulfonamide with 16.0 grams (0.131 mole) of isopropyl chlorocarbonate in the presence of 18.8 grams (0.136 mole) of anhydrous $K_2CO_3$ and 200 ml. dry acetone according to the procedure described in Example XIV except that the solid from the acetone filtrate was dissolved in 100 ml. ether instead of isopropanol. The ether extract was then heated under vacuum to remove the ether and leave a clear colorless oil which solidified on cooling. This solid was the carbamate product. Weight of the product was 11.4 grams which represented a yield of 60%. The product was recrystallized from a water-alcohol solvent (10 ml. water + 35 ml. 95% alcohol/5% water). Sintering point was 65°C; melting point was 70°–72°C.

EXAMPLE XVI

In this example, the herbicidal activity of the N-(arylsulfonyl) carbamates is demonstrated. Table I presents data showing the herbicidal activity of some of the subject carbamates upon selected plant systems at various rates of application in a pre-emergent application to the soil wherein seeds of these plants are present. The Roman numerals represent selected N-(arylsulfonyl) carbamates where:

I = Ethyl N-(p-nitrobenzenesulfonyl) carbamate;
II = Ethyl N-(p-chlorobenzenesulfonyl) carbamate;
III = Ethyl N-(benzenesulfonyl) carbamate;
IV = Allyl N-(m-nitrobenzenesulfonyl) carbamate;
V = Allyl N-(p-toluenesulfonyl) carbamate;
VI = Allyl N-(p-chlorobenzenesulfonyl) carbamate;
VII = Allyl N-(3,4-dichlorobenzenesulfonyl) carbamate;
VIII = Methyl N-(benzenesulfonyl) carbamate;
IX = Isopropyl N-(p-toluenesulfonyl) carbamate;
X = Isopropyl N-methyl-N-(p-toluenesulfonyl) carbamate;
XI = Isopropyl N-benzyl-N-(p-toluenesulfonyl) carbamate;
XII = Isopropyl N-(p-chlorobenzenesulfonyl) carbamate; and
XIII = Dimethylamine salt of ethyl (p-nitrobenzenesulfonyl) carbamate The plants on which the above carbamates were tested are designated in Table I as follows:

| | | |
|---|---|---|
| A = grass | F = rye grass | K = pigweed |
| B = broadleaf | G = radish | L = soybean |
| C = morning glory | H = sugar beet | M = wild buckwheat |
| D = wild oat | I = foxtail | N = tomato |
| E = brome grass | J = crab grass | O = sorghum |

The testing procedure used in the evaluation of pre-emergence activity is as follows. A good grade of topsoil was placed in either 9½ inches × 5¾ inches × 2¾ inches or 9 inches × 13 inches × 2 inches aluminum pans and compacted to a depth of three-eighth inches from the top of the pan. On top of the soil were placed a designated number of seeds of radish, morning glory, tomato, sugar beet, sorghum, brome grass, wild buckwheat, giant foxtail, rye grass, wild oat, pigweed, crab grass, and soybean. Two different chemical applications were made; one wherein the herbicidal composition was applied to the surface of the soil and the other wherein the composition was admixed with or incorporated in the top layer of soil. For the surface application, the seeds were then covered with three-eighth inch of prepared soil mixture and the pan leveled. In the soil-incorporation plantings, a weighed amount of prepared soil mixture was blended with the herbicide composition in a separate mixing container, and this blend was then used to cover the seeds. The surface application of the herbicide composition was made by spraying the surface of the soil with a solvent solution containing a sufficient quantity of the subject carbamate to obtain the desired rate per acre on the soil surface. The watering of the seeds in both type plantings were accomplished by placing the aluminum pans in a sand bench bringing the water level to one-half inch depth of water thereon and permitting the soil in the pans to absorb moisture through the perforated bottoms of the pans and the excess water to drain through an opening in the bottom of the bench.

The planted pans were maintained there for 14 days under ordinary conditions of sunlight and watering. At the end of this time, the plants were observed and the results recorded by counting the number of plants of each species which germinated and grew. The herbicidal rating was obtained by means of a fixed scale based on the average percent germination of each seed lot. Herbicidal activity is indicated according to the following scale:

0 = no phytotoxicity
1 = slight phytotoxicity
2 = moderate phytotoxicity
3 = severe phytotoxicity

TABLE 1

|   |   | A | B | C | D | E | F | G | H | I | J | K | L | M | N | O |
|---|---|---|---|---|---|---|---|---|---|---|---|---|---|---|---|---|
| I | 25 lbs./a | 2 | 1 | 2 | 2 | 3 | 2 | 3 | 2 | 3 | 3 | 3 | 0 | 3 | 2 | 3 |
|   | *5 lbs./a | 3 | 2 | 0 | 2 | 3 | 3 | 3 | 2 | 3 | 3 | 2 | 1 | 2 | 0 | 3 |
|   | *1 lb./a | 2 | 0 | 0 | 0 | 1 | 1 | 3 | 0 | 3 | 3 | 0 | 0 | 0 | 0 | 2 |
| II | 25 lbs./a | 2 | 0 | 3 | 1 | 1 | 2 | 3 | 3 | 2 | 2 | 3 | 0 | 3 | 2 | 3 |
|   | 5 lbs./a | 0 | 0 | 0 | 0 | 3 | 0 | 0 | 0 | 0 | 0 | 0 | 0 | 3 | 0 | 0 |
|   | 1 lb./a | 0 | 0 | 0 | 0 | 0 | 0 | 0 | 0 | 0 | 0 | 0 | 0 | 1 | 0 | 0 |
| III | 25 lbs./a | 1 | 0 | 0 | 0 | 1 | 1 | 0 | 0 | 3 | 3 | 3 | 0 | 0 | 0 | 2 |
|   | 5 lbs./a | 0 | 0 | 0 | 0 | 0 | 0 | 0 | 0 | 0 | 0 | 0 | 0 | 0 | 0 | 0 |
|   | *5 lbs./a | 0 | 2 | 3 | 0 | 0 | 0 | 0 | 1 | 0 | 1 | 3 | 0 | 0 | 2 | 1 |
| IV | 25 lbs./a | 0 | 2 | 3 | 0 | 0 | 0 | 0 | 3 | 1 | 0 | 3 | 3 | 1 | 3 | 0 |
|   | 5 lbs./a | 0 | 2 | 0 | 0 | 0 | 0 | 1 | 2 | 0 | 0 | 1 | 3 | 0 | 3 | 0 |
|   | *1 lb./a | 0 | 0 | 0 | 0 | 0 | 0 | 0 | 0 | 0 | 0 | 0 | 0 | 0 | 0 | 0 |
| V | 5 lbs./a | 0 | 1 | 0 | 0 | 0 | 0 | 2 | 3 | 0 | 0 | 2 | 0 | 0 | 0 | 0 |
| VI | 25 lbs./a | 2 | 2 | 1 | 0 | 0 | 1 | 2 | 2 | 2 | 3 | 3 | 0 | 3 | 3 | 3 |
|   | 5 lbs./a | 0 | 0 | 0 | 0 | 0 | 0 | 0 | 0 | 0 | 0 | 0 | 0 | 0 | 0 | 0 |
| VII | 25 lbs./a | 2 | 2 | 0 | 0 | 0 | 2 | 3 | 3 | 3 | 3 | 3 | 0 | 2 | 0 | 3 |
|   | 5 lbs./a | 0 | 0 | 0 | 0 | 0 | 0 | 0 | 0 | 0 | 0 | 0 | 0 | 0 | 0 | 0 |
| VIII | 25 lbs./a | 3 | 2 | 0 | 3 | 3 | 2 | 3 | 3 | — | 3 | 3 | 0 | 3 | 3 | 1 |
|   | *5 lbs./a | 3 | 2 | 1 | 3 | 3 | 1 | 3 | 3 | 1 | 3 | 3 | 1 | 2 | 3 | 1 |
|   | *1 lb./a | 1 | 0 | 1 | 2 | 1 | 0 | 1 | 1 | 0 | 2 | 1 | 1 | 0 | 1 | 1 |
| IX | 25 lbs./a | 0 | 1 | 0 | 0 | 0 | 1 | 0 | 0 | 0 | 0 | 3 | 1 | 3 | 1 | 0 |
|   | 10 lbs./a | 0 | 0 | 0 | 0 | 0 | 0 | — | 0 | 0 | 0 | 1 | 0 | 0 | 0 | 0 |
|   | *5 lbs./a | 0 | 0 | 0 | 0 | 0 | 0 | 0 | 0 | 0 | 0 | 3 | 0 | 0 | 0 | 0 |
| X | 25 lbs./a | 0 | 1 | 1 | 0 | 0 | 0 | 0 | 2 | 2 | 2 | 3 | 0 | 0 | 0 | 0 |
|   | 10 lbs./a | 0 | 0 | 0 | 0 | 0 | 0 | 0 | 2 | 1 | 2 | 1 | 0 | 0 | 0 | 0 |
|   | *5 lbs./a | 0 | 0 | 0 | 0 | 0 | 0 | 0 | 0 | 0 | 2 | 0 | 0 | 0 | 0 | 0 |
| XI | 25 lbs./a | 0 | 0 | 0 | 0 | 0 | 0 | 0 | 3 | 2 | 2 | 2 | 0 | 0 | 0 | 0 |
|   | 10 lbs./a | 0 | 0 | 0 | 0 | 0 | 0 | 0 | 0 | 1 | 1 | 0 | 0 | 0 | 0 | 0 |
|   | *5 lbs./a | 0 | 1 | 0 | 0 | 0 | 0 | 1 | 0 | 1 | 3 | 3 | 0 | 0 | 0 | 1 |
| XII | 25 lbs./a | 2 | 3 | 2 | 1 | 2 | 2 | 3 | 3 | 3 | 2 | 3 | 1 | 1 | 3 | 2 |
|   | 10 lbs./a | 1 | 2 | 0 | 0 | 0 | 0 | 3 | 3 | 3 | 1 | 3 | 1 | 0 | 1 | 1 |
|   | *5 lbs./a | 0 | 0 | 0 | 0 | 0 | 0 | 0 | 0 | 0 | 0 | 1 | 0 | 0 | 0 | 1 |
| XIII | 25 lbs./a | 3 | 1 | 0 | 3 | 3 | 2 | 3 | 2 | 3 | 3 | 3 | 0 | 0 | 0 | 3 |
|   | *5 lbs./a | 3 | 0 | 0 | 0 | 3 | 3 | 3 | 0 | 3 | 3 | 2 | 0 | 0 | 0 | 3 |
|   | *1 lbs./a | 0 | 0 | 0 | 0 | 1 | 0 | 3 | 0 | 1 | 2 | 0 | 0 | 0 | 0 | 0 |

*Incorporation into top soil; treatments not marked with an asterisk are surface applications.

EXAMPLE XVII

In this example, the contact herbicidal activity of the same N-(arylsulfonyl) carbamates was determined in greenhouse tests. The carbamate to be tested was applied in spray form to 21-day old specimens of the same grasses and broadleaf plant as used in the pre-emergence tests described in Example XVI. The same number of seeds of the same plants used in Example XVI were planted in the 9½ inches × 5¾ inches × 2¾ inches aluminum pans arranged in the same manner with a soybean seed in diagonal corners. After the plants were 21 days old, they were sprayed with six ml. of a 0.5% solution of the subject carbamate which corresponds to a rate of approximately 9 lbs. per acres. Ethyl N-(n-butyl) N-(benzenesulfonyl) carbamate and allyl N-(p-toluenesulfonyl) carbamate showed no contact herbicidal activity. Slight contact herbicidal activity was shown by ethyl N-(p-nitrobenzenesulfonyl) carbamate, ethyl N-(p-chlorobenzenesulfonyl) carbamate, allyl N-(m-nitrobenzenesulfonyl) carbamate, and allyl N-(p-chlorobenzenesulfonyl) carbamate. Moderate contact herbicidal activity was exhibited by allyl N-(3,4-dichlorobenzenesulfonyl) carbamate. Good contact herbicidal activity at 0.2% was shown by the dimethylamine salt of ethyl N-(p-nitrobenzenesulfonyl) carbamate.

The herbicidally active compounds of this invention are either solid or liquid materials, depending upon the particular substituents present in the compounds. To aid in achieving a uniform distribution of the active compounds over the entire area of the soil or plants to be treated, it is often disadvantageous to employ a composition comprising a diluent or extending agent in addition to the active compounds. Suitable solid extending agents are those which render the compositions permanently dry and free flowing. Therefore hygroscopic materials are not preferred extending agents unless there is included in the composition a separate substance to aid flowability. Effective solid diluents include natural clays, such as china clays, bentonites, and the attapulgites; other minerals in their natural state such as talc, pyrophylite, quartz, diatomaceous earth, Fuller's earth, chalk, rock phosphate, and sulfur; and chemically modified minerals, such as acid-washed bentonite, precipitated calcium phosphate, precipitated calcium carbonate, and colloidal silica. These diluents may represent a substantial portion, e.g. 50 to 98 percent by weight of the entire formulation as applied to plant or soil. Formulations more concentrated with respect to the active ingredient may be prepared, but they will usually require additional dilution by the user in order to properly prepare the composition for the most effective usage. Therefore the toxicant formulation as applied in the field will normally consist of a minor amount, i.e. less than 50% by weight of the entire formulation, of the N-(arylsulfonyl) carbamate and a major amount, or more than 50% of the entire formulation, of an adjuvant or adjuvants.

Liquid extending agents are also useful in the practice of this invention. The N-(arylsulfonyl) carbamates of this invention are insoluble in water and are readily soluble in most organic solvents. Therefore the choice of a liquid extending agent is quite variable if a solution of the active ingredients is desired. In addition the active compounds need not be dissolved but merely dispersed in the extending agent in the form of a suspension of emulsion. One method of forming this dispersion is to dissolve the N-(arylsulfonyl) carbamate in a suitable organic solvent and then add this solution to water or some other liquid extending agent to form the dispersion. Examples of some organic solvents suitable for use as extending agents when a solution is desired include: ethers such as ethyl ether, isopropylether, n-propyl ether; alcohols such as ethyl, isopropyl, n-propyl, and butyl alcohols; ketones such as acetone, methylethyl ketone, and cyclohexanone; aromatic hydrocarbons such as benzene, toluene, xylene and cumene. Solvents useful as extending agents when a dispersion of the active compound in the solvent is acceptable include: water, hexane, and other aliphatic hydrocarbons.

The incorporation of a surface active agent into the herbicidal formulation is an aid helpful in forming uniform dispersions or emulsions of the active N-(arylsulfonyl) carbamates in water. This surface wetting agent, that is the wetting, emulsifying, or dispersion agent, may be either anionic, cationic, non-ionic, or mixtures thereof. Suitable wetting agents are the organic compounds capable of lowering the surface tension of water and include the conventional soaps such as the water-soluble salts of long-chain carboxylic acids; the amino soaps such as the amine salts of long-chain carboxylic acids; the sulfonated animal, vegetable, and mineral oils; quaternary salts of high molecular weight acids; rosin soaps such as salts of abietic acid; sulfuric acid salts of high molecular weight organic compounds; algin soaps; and simple and polymeric compositions having both hydrophilic and hydrophobic functions.

Concentrated compositions of the N-arylsulfonyl carbamates ordinarily have the active ingredient and the surface active agent present in higher concentrations than the toxicant compositions applied in the field so that upon dilution with an extending agent, compositions containing optimum proportions of active ingredient and surface active agent are prepared to obtain uniform distribution and to maintain the active ingredient in a form enabling prompt assimilation by the plants.

The concentrate compositions preferably comprise 5% to 95% by weight of the active ingredient, the remainder consisting of the adjuvant. If a liquid concentrate is desired, this adjuvant may be solely liquid extending agent or surface active agent, but preferably is a combination of the two. Preferably the surface active agent comprises from 0.1% to 15% of the concentrate, and the liquid extender comprises from 5% to 95% of the concentrate. If a solid concentrate is desired, the adjuvant is usually made up solely of a solid extender unless the dust concentrate is to be applied as a wettable powder, in which case an amount of surface active agent comparable to that used in the liquid formulation, that is 0.1% to 15%, may be desirable.

Carrier materials or diluents necessary to dilute the concentrates to a toxicological level suitable for plant control may be either a liquid or particulate solid. Materials mentioned previously as extenders may also be used as carriers; however the use of some of these materials as carriers is often not economically feasible. Water is a preferred liquid carrier; suitable solid carriers include solid fertilizers such as ammonium nitrate, urea, and superphosphate, as well as other materials in which plant organisms may take root and grow such as compost, manure, humus, and sand.

In addition to the above described conditioning agents, other adjuvants may be added, such as insecticides, fungicides, nematocides and other herbicides of a supplementary nature. This may be done when it is desired to broaden the spectrum of activity to include problem weeds, insects, or fungi.

The herbicidal compositions containing the N-arylsulfonyl carbamates are applied to the plant systems in the conventional manner. Thus, the dust and liquid compositions may be applied to the foliage of growing plants or to the soil by the use of power-operated dusters and sprayers as well as manually operated devices. Some of the compounds of this invention provide superior protection and control when mixed with the top few inches of soil. This can be accomplished by addition of the composition to irrigation water supplied to the field to be treated. Dust compositions sprinkled on the surface of the soil can be distributed below the surface by the usual discing, dragging, or mixing operations.

The application of a herbicidally effective amount of the N-(arylsulfonyl) carbamate to the area to be controlled is essential to the practice of this invention. The exact dosage to be applied is dependent not only upon the specific carbamate but also upon the particular type of protection desired. As a general rule, the pre-emergence herbicidal activity of the N-(arylsulfonyl) carbamates is the most significant although the post-emergence activity is quite pronounced for some compounds. Herbicidal activity is usually achieved by application of the N-(arylsulfonyl) carbamates at a rate of from about 1 to about 50 pounds per acre. However lower rates of application may be required with some of the carbamates, particularly if a herbicidally selective activity is desired.

The herbicidally active compounds of this invention have been described in terms of specific groups of types of N-(arylsulfonyl) carbamates. However it should be noted that this invention is intended to cover these compounds in which the substituent groups (the X, Y, Z, R, and $R_1$ radicals) can also contain constituents other than those mentioned if these constituents do not interfere with the biological activity of the parent N-(arylsulfonyl) carbamate. Those skilled in the art will recognize that a compound containing a hydrocarbon radical that is substituted with a non-interfering group is the equivalent of the corresponding compound containing a nonsubstituted hydrocarbon radical. Such a non-interfering group can be initially present in the compound subjected to one of the reactions of this invention and can, depending on circumstances, either be retained in the product molecular or be destroyed or changed during the reaction; or such group can be introduced by known means into one of the new compounds of this invention subsequent to the formation of such compound. Accordingly, these and other modifications are contemplated which can be made without departing from the spirit of the described invention.

What is claimed is:

1. An amine salt, alkali metal salt or alkaline earth metal salt of a N-benzenesulfonyl carbamate of the formula

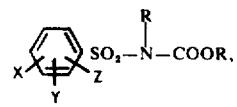

where X, Y, and Z are selected from the group consisting of hydrogen, chloro, bromo, iodo, nitro, and lower alkyl; where R is selected from the group consisting of hydrogen, alkyl, cycloalkyl, alkenyl, alkynyl, aryl, alkaryl, aralkyl having up to 8 carbon atoms and lower alkanoyl; and where $R_1$ is selected from the group consisting of alkyl, cycloalkyl, alkenyl, alkynyl, aryl, alkaryl and aralkyl having up to 8 carbon atoms.

2. Lower alkenyl N-benzenesulfonyl carbamate.
3. Isopropyl N-benzenesulfonyl carbamate.
4. Dimethylamine salt of ethyl N-(p-nitrobenzenesulfonyl) carbamate.